US010568822B2

(12) United States Patent
Kondo et al.

(10) Patent No.: US 10,568,822 B2
(45) Date of Patent: Feb. 25, 2020

(54) MELANOGENESIS INHIBITOR COMPRISING D-PANTOTHENYL ALCOHOL, AND SKIN-WHITENING COSMETIC CONTAINING SAME MELANOGENESIS INHIBITOR

(71) Applicant: POLA CHEMICAL INDUSTRIES, INC., Shizuoka (JP)

(72) Inventors: Chihiro Kondo, Yokohama (JP); Shoko Sassa, Yokohama (JP); Yuko Saitoh, Yokohama (JP); Yasuhito Mori, Yokohama (JP); Kouji Yokoyama, Yokohama (JP)

(73) Assignee: POLA CHEMICAL INDUSTRIES, INC., Fukuroi-Shi, Shizuoka (JP)

(*) Notice: Subject to any disclaimer, the term of this patent is extended or adjusted under 35 U.S.C. 154(b) by 0 days.

(21) Appl. No.: 15/129,391

(22) PCT Filed: Apr. 2, 2015

(86) PCT No.: PCT/JP2015/060519
§ 371 (c)(1),
(2) Date: Sep. 27, 2016

(87) PCT Pub. No.: WO2015/152384
PCT Pub. Date: Oct. 8, 2015

(65) Prior Publication Data
US 2017/0119638 A1 May 4, 2017

(30) Foreign Application Priority Data
Apr. 3, 2014 (JP) ................. 2014-076693

(51) Int. Cl.
A61K 8/42 (2006.01)
A61K 8/34 (2006.01)
A61K 8/49 (2006.01)
A61Q 19/02 (2006.01)
A61K 8/33 (2006.01)
A61K 8/37 (2006.01)
A61K 8/92 (2006.01)
A61K 8/97 (2017.01)

(52) U.S. Cl.
CPC .............. A61K 8/42 (2013.01); A61K 8/33 (2013.01); A61K 8/34 (2013.01); A61K 8/345 (2013.01); A61K 8/37 (2013.01); A61K 8/4973 (2013.01); A61K 8/92 (2013.01); A61K 8/97 (2013.01); A61Q 19/02 (2013.01); A61K 2800/782 (2013.01)

(58) Field of Classification Search
CPC .................... A61K 8/34; A61Q 91/02
See application file for complete search history.

(56) References Cited

U.S. PATENT DOCUMENTS

2005/0129618 A1* 6/2005 Ashida ................ A61K 8/97
424/9.2
2007/0299137 A1* 12/2007 Comini ................ A61K 8/44
514/574
2009/0075946 A1 3/2009 Ochiai et al.
2009/0181926 A1 7/2009 Akamatsu et al.
2011/0243865 A1 10/2011 Yokoyama et al.
2011/0245343 A1 10/2011 Suenobu et al.
2012/0258063 A1 10/2012 Saitoh et al.
2012/0282203 A1* 11/2012 Yamasaki ............ A61K 8/466
424/62

FOREIGN PATENT DOCUMENTS

| CA | 2827499 A1 | 3/2014 |
|---|---|---|
| CH | 710622 A2 | 7/2016 |
| CN | 101467954 A | 7/2009 |
| CN | 101851171 A | 10/2010 |
| JP | 2001-335461 A | 12/2001 |
| JP | 2002-205913 A | 7/2002 |
| JP | 2003-081746 A | 3/2003 |
| JP | 2003-246722 A | 9/2003 |
| JP | 2004-107262 A | 4/2004 |
| JP | 2006-193495 A | 7/2006 |
| JP | 2007-176810 A | 7/2007 |
| JP | 2007-308516 A | 11/2007 |
| JP | 2011-241164 A | 12/2011 |
| JP | 2012-41302 A | 3/2012 |
| JP | 2012-167042 A | 9/2012 |
| KR | 10-0751883 B1 | 8/2007 |
| KR | 10-2011-0001538 A1 | 1/2011 |
| WO | WO 2006/132033 A1 | 12/2006 |
| WO | WO 2007/148472 A1 | 12/2007 |
| WO | WO 2010/058730 A1 | 5/2010 |
| WO | WO 2010/074052 A1 | 7/2010 |
| WO | WO 2011/074643 A1 | 6/2011 |

OTHER PUBLICATIONS

International Search Report issued in International Application No. PCT/JP2015/060519, dated Jul. 7, 2015.
English Translation of International Preliminary Report on Patentability issued by the International Bureau of WIPO dated Oct. 4, 2016 in the corresponding PCT Application No. PCT/JP2015/060519—6 pages.
Extended European Search Report issued in European Patent Application No. 15774137.2 dated Oct. 25, 2017.
Anti-Aging Reconstruction Cream, Database GNPD [Online] Mintel, Accession No. 2020999, Mar. 1, 2013.
Anti-Aging Body Lotion, Database GNPD [Online] Mintel, Accession No. 2294289, Feb. 1, 2014.
Brightening Eye Cream, Database GNPD [Online] Mintel, Accession No. 1855135, Aug. 1, 2012.
Lotion, Database GNPD [Online] Mintel, Accession No. 1848478, Jul. 1, 2012.
Belikov, V.G., Pharmaceutical Chemistry, M., Higher Education, 1993, pp. 43 to 47.

(Continued)

Primary Examiner — Kyle A Purdy
(74) Attorney, Agent, or Firm — Knobbe, Martens, Olson & Bear LLP

(57) ABSTRACT

Provided is a new application for D-pantothenyl alcohol. It is a melanogenesis inhibitor comprising D-pantothenyl alcohol.

5 Claims, 1 Drawing Sheet

(56) References Cited

OTHER PUBLICATIONS

Korean Office Action in corresponding Korean Patent Application No. 10-2016-7027811, dated Mar. 15, 2018 with English Translation.
Russian Office Action in corresponding Russian Patent Application No. 2016143096, dated Feb. 27, 2018 with English Translation.
Notification of Reasons for Refusal received in corresponding Japanese Patent Application No. 2016-512004 dated Jan. 8, 2019.
Kobayashi, D., et al., "The Effect of Pantothenic Acid Deficiency on Keratinocyte Proliferation and the Synthesis of Keratinocyte Growth Factor and Collagen in Fibroblasts", Journal of Pharmacological Sciences 115:230-234, 2011.
Partial European Search Report issued in corresponding European Patent Application No. 19170601.9 dated Jul. 26, 2019.
Database GNPD [Online], Mintel, Day Cover Whitening Vitamin Cream SPF 15, Database Accession No. 2130624, Jul. 24, 2013.
Database GNPD [Online], Mintel, Perfect White Eye Serum, Database Accession No. 2100918, Jun. 20, 2013.
Database GNPD [Online], Mintel, Whitening Face Lotion, Database Accession No. 1537841, May 17, 2011.
Office Action issued in connection with corresponding Taiwan Patent Application No. 104111108 dated Jul. 10, 2019.
Office Action issued in corresponding Canadian Patent Application No. 3,007,176 dated Apr. 18, 2019.
Office Action issued in corresponding European Patent Application No. 15774137.2 dated May 6, 2019.
Database GNPD [Online] Mintel, Rose Brightening Mud Mask, Record ID 1876687, Sep. 26, 2012.
Database GNPD [Online] Mintel, Discoloration Reversal Moisturizer, Record ID 1854382, Sep. 13, 2012.
Office Action dated Oct. 29, 2019, in Japanese Patent Application No. 2016-512004.
Data Base GNPD [Online], MINTEL, Pore Minimiser Foam 10in1, Database Accession No. 1791162, 2012.
Data Base GNPD [Online], MINTEL, Clinical Regenerating Night Care, Database Accession No. 1830313, 2012.
Data Base GNPD [Online], MINTEL, Clarifying Facial Foam, Database Accession No. 1884783, 2012.
Data Base GNPD [Online], MINTEL, Spot Eraser, Database Accession No. 2375815, 2014.

\* cited by examiner

MELANOGENESIS INHIBITOR COMPRISING D-PANTOTHENYL ALCOHOL, AND SKIN-WHITENING COSMETIC CONTAINING SAME MELANOGENESIS INHIBITOR

CROSS-REFERENCE TO RELATED APPLICATIONS

This application is the U.S. National Phase under 35 U.S.C. § 371 of International Application PCT/JP2015/060519, filed Apr. 2, 2015, which claims priority to JP 2014-076693, filed Apr. 3, 2014.

TECHNICAL FIELD

The present invention relates to a melanogenesis inhibitor containing D-pantothenyl alcohol. The present invention also relates to a skin-whitening cosmetic containing the melanogenesis inhibitor.

BACKGROUND ART

D-pantothenyl alcohol is an alcohol type derivative of a pantothenic acid and is a substance that is converted into vitamin B5 (pantothenic acid) in the body. It has also been used as a material for skin external preparations since long ago, and many skin external preparations containing D-pantothenyl alcohol have been proposed.

For example, Patent Literature 1 mentions that a skin cosmetic containing D-pantothenyl alcohol improves rough skin, particularly dry skin, and conditions skin quality.

Patent Literature 2 also mentions that a hair cosmetic containing D-pantothenyl alcohol makes the firmness, body, and smoothness of hair better.

CITATION LIST

Patent Literature

Patent Literature 1: Japanese Patent Application Laid-Open No. 2012-41302
Patent Literature 2: Japanese Patent Application Laid-Open No. 2012-167042

SUMMARY OF INVENTION

Technical Problem

The present invention provides a new application for the aforementioned D-pantothenyl alcohol.

Solution to Problem

The present inventors have found from experiments that D-pantothenyl alcohol has a melanogenesis inhibitory action, and have completed the present invention. In other words, a first aspect of the present invention is a melanogenesis inhibitor containing D-pantothenyl alcohol. Another aspect of the present invention is a skin-whitening cosmetic containing the aforementioned melanogenesis inhibitor.

Advantageous Effects of Invention

According to the present invention, a new melanogenesis inhibitor is provided. Moreover, according to another aspect of the present invention, a skin-whitening cosmetic having a high skin-whitening effect is provided.

DESCRIPTION OF EMBODIMENTS

The present invention will be described below in detail, and of course, the present invention is not limited to only the specific embodiments.

D-pantothenyl alcohol is a compound represented by the following structural formula (1).

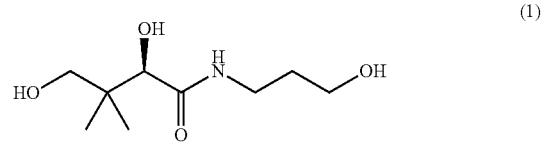

(1)

D-pantothenyl alcohol is used as a material for skin external preparations such as cosmetics, there is no difficulty in availability, and it is possible to use a commercially available product as appropriate.

The present inventors conducted the experiments described below, and have found from the results that D-pantothenyl alcohol has a melanogenesis inhibitory action in addition to a keratinocyte cell proliferation action.

Experiment 1: Melanogenesis Inhibition Experiment

According to the method described below, 2-thiouracil ($^{14}$C-labeled 2-thiouracil in the present test) which is specifically incorporated into melanin in the melanin synthesis process within cells was used to evaluate the melanogenesis inhibitory action. With a complete medium for melanocyte culture (Invitrogen Corporation) used in a 24-well plate, human normal melanocytes (Kurabo Industries, Ltd.) were seeded in each well at a concentration of $6.0 \times 10^4$ cells/well/0.5 mL. Under a 5% carbon dioxide atmosphere, the culture was conducted at 37° C. for 24 hours. Then, replacement was made such that a 0.5 mL medium containing D-pantothenyl alcohol at 0 mM or 1 mM was in each of three wells for each concentration and, to these nine wells, 0.5 µCi/well of 2-[2-$^{14}$C] thiouracil (Daiichi Clarity Co., Ltd.) was further added. And it was further cultured for 3 days under the same conditions as the aforementioned culture conditions. After completion of the culture, the culture medium was removed from each well, which was washed with PBS (phosphate-buffered saline), and the number of cells was measured using the WST-8 reagent (Dojindo Laboratories). The WST-8 reagent was removed from each well, which was washed with PBS, and using 100 (w/v) % trichloroacetic acid (Wako Pure Chemical Industries, Ltd.), the cells were separated from the bottom of the wells, to which water was then added for dilution so that the concentration of the trichloroacetic acid could be 10 (w/v) %, and which were allowed to stand in a refrigerator for 30 minutes. After the cells were recovered by centrifugation, the amount of $^{14}$C- thiouracil in the cells recovered from each well was measured with a liquid scintillation counter (Aloka Co., Ltd.).

Figure 1:
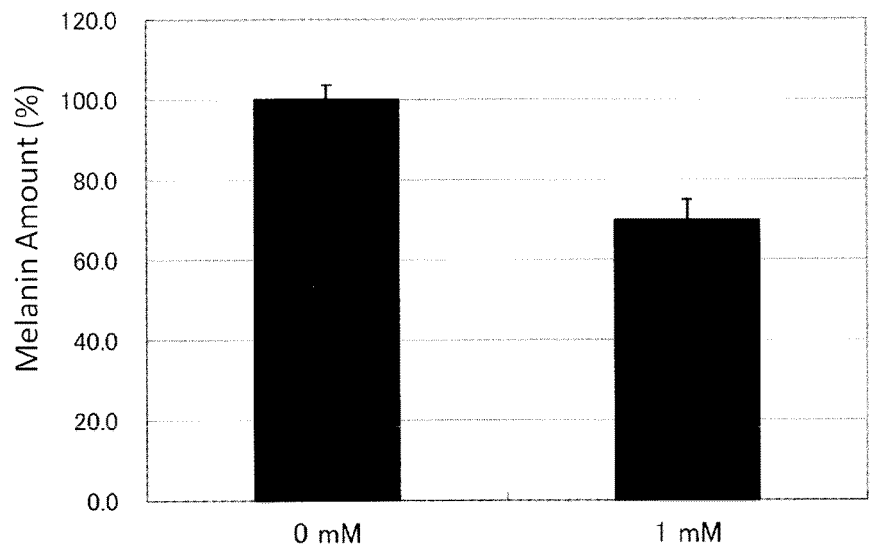
FIG. 1 is a graph illustrating a melanogenesis inhibitory action of D-pantothenyl alcohol in an experimental example.

Relative to the radiation doses of the cells cultured in the media containing 0 mM D-pantothenyl alcohol (control), the radiation doses of the cells cultured in the media containing 1 mM D-pantothenyl alcohol were each obtained in percentage as the amount of melanin (%). In other words, it is possible to determine that the smaller the radiation dose incorporated into each cell is, the smaller the amount of melanin is, and accordingly, it is possible to determine that the melanin inhibition titer of the added ingredient is larger. The results are shown in FIG. 1.

Experiment 2: Keratinocyte Cell Proliferation Experiment

According to the method described below, the cell proliferation promoting action was evaluated. With a complete medium for keratinocyte culture (Kurabo Industries, Ltd.) used in a 24-well plate, human normal keratinocytes (Kurabo Industries, Ltd.) were seeded in each well at a concentration of $1.0 \times 10^4$ cells/well/1 mL. Under a 5% carbon dioxide atmosphere, the culture was conducted at 37° C. for 24 hours. Then, replacement was made such that a 1 mL medium containing D-pantothenyl alcohol at 0 μM, 15 μM, or 150 μM was in each of three wells for each concentration. And it was further cultured for 2 days under the same conditions as the aforementioned culture conditions. After completion of the culture, 20 μL of the WST-8 reagent (Dojindo Laboratories) was added to each well, and color reaction was allowed at 37° C. for 3 hours. After the reaction, absorbances at 450 nm and 650 nm were measured using a microplate reader, Benchmark Plus (Bio-Rad Laboratories), and the 450 nm absorbance measurement minus the 650 nm absorbance measurement was calculated to give a cell proliferation measurement.

Figure 2:
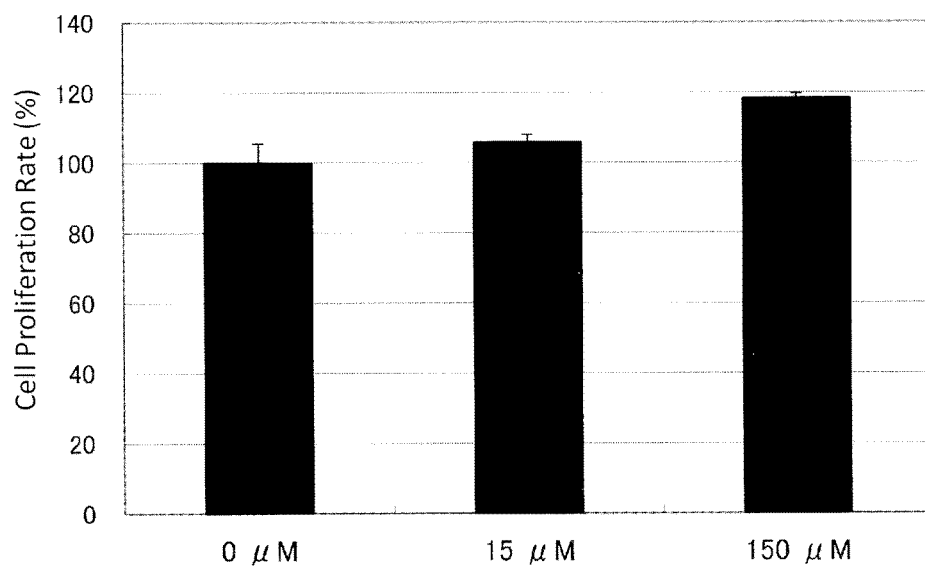
FIG. 2 is a graph illustrating a keratinocyte cell proliferation action of D-pantothenyl alcohol in an experimental example.

Relative to the cell proliferation measurements for the wells cultured in the media containing 0 μM D-pantothenyl alcohol (control), the cell proliferation measurements for the wells cultured in the media containing D-pantothenyl alcohol were each obtained in percentage as a cell proliferation rate (%). In other words, it is possible to determine that the larger the absorbance value is, the higher the cell proliferation rate is, and accordingly, it is possible to determine that the cell proliferation promotion titer of the added ingredients is larger. The results are shown in FIG. 2.

It is recognized from the aforementioned Experiment 1 that D-pantothenyl alcohol has a melanogenesis inhibitory action and is a material having a skin-whitening effect.

It is also recognized from the aforementioned experiment 2 that D-pantothenyl alcohol also has a keratinocyte cell proliferation action, and the keratinocyte cell proliferation is considered to promote turnover of keratinocytes and to promote melanin discharge.

It is recognized from the aforementioned experiments that D-pantothenyl alcohol not only inhibits melanogenesis but also promotes melanin discharge, and through the skin-whitening action by such two action mechanisms, D-pantothenyl alcohol achieves a high skin-whitening effect. Furthermore, having the two action mechanisms, particularly having the turnover promoting action of keratinocytes, can be expected to allow a faster skin-whitening effect to be obtained (faster skin-whitening rate) compared to conventional skin-whitening agents. In addition, having such action mechanisms different from those of conventional skin-whitening agents, with combined use of other skin-whitening agents, can be expected to allow a skin-whitening effect durability and a higher skin-whitening effect.

Thus, since D-pantothenyl alcohol achieves a high skin-whitening effect, it is preferably formulated into skin-whitening cosmetics. It is also preferably formulated as an effective ingredient into skin-whitening cosmetics. When D-pantothenyl alcohol is formulated into skin-whitening cosmetics, the amount of formulation is usually 0.0001% by mass or more, preferably 0.001% by mass or more, more preferably 0.01% by mass or more, still more preferably 0.1% by mass or more. Meanwhile, the upper limit is usually 20% by mass or less, preferably 10% by mass or less, more preferably 5% by mass or less.

Examples of an aspect of applying D-pantothenyl alcohol to the skin include, for example, a method for applying it in combination with a plant extract having a melanogenesis inhibitory action. The skin-whitening effect of D-pantothenyl alcohol can be significantly enhanced in combination with a plant extract having a melanogenesis inhibitory action. Preferable examples of plant extracts can include *Uncaria gambir* extract, *Isodon japonicus* extract, *Echinacea angustifolia* leaf extract, *Lithospermum erythrorhizon* root extract, *Carthamus tinctorius* flower extract, *Persea gratissima* fruit extract, *Abelmoschus esclentus* fruit extract, *Actinidia chinensis* fruit extract, *Alpinia speciosa* leaf extract, *Saponaria officinalis* extract, *Caprifoliaceae* extract, green tea extract, *Benincasa cerifera* seed extract, *Allium sativum* extract, *Citrus aurantifolia* fruit juice extract, natto extract, *Citrus aurantium* dulsis fruit extract, *Valeriana officinalis* extract, *Cucumis sativus* extract, *Prunus armeniaca* extract, *Gardenia florida* extract, *Citrus grandis* fruit extract, *Arctium lappa* root extract, black tea extract, *Equisetum arvense* extract, *Malva sylvestris* extract, *Jujube* extract, *Solanum lycopersicum* extract, *Daucus carota sativa* extract, *Hoelen* extract, *Lilium candidum* bulb extract, *Litchi chinensis* extract, *Lactuca scariola sativa* leaf extract, *Citrus medica limonum* fruit extract, royal jelly extract, and the like. Among these plant extracts, one species alone may be used, or a combination of two or more species may be used.

When a plant extract having a melanogenesis inhibitory action and D-pantothenyl alcohol are applied to the skin, they are preferably applied simultaneously or nearly simultaneously. As used herein, "nearly simultaneously" refers to, for example, within one day, more preferably within 12 hours, more preferably within 6 hours, particularly preferably within 1 hour.

Specifically, preferable examples can include a method in which both are formulated in a skin external preparation and are applied to the skin as effective ingredients of the skin external preparation.

Such an applying method can be adapted to a skin-whitening method in which a skin-whitening ingredient other than a plant extract and D-pantothenyl alcohol are combined.

When a plant extract having a melanogenesis inhibitory action is formulated into a skin-whitening cosmetic, the amount of formulation is usually 0.0001% by mass or more, preferably 0.001% by mass or more, more preferably 0.01% by mass or more, still more preferably 0.1% by mass or more. Meanwhile, the upper limit is usually 20% by mass or less, preferably 10% by mass or less, more preferably 5% by mass or less.

Methods for extracting these plant extracts are not particularly limited, and preferably include an extracting method using a solvent. When the extraction is conducted, the aforementioned raw materials may be used directly, whereas those pulverized and shredded into powder to be served for extraction allows the effective ingredient to be extracted at a higher extraction efficiency under milder conditions in a shorter period of time.

The extraction temperature is not particularly limited and may be appropriately set in accordance with the size, solvent type, and the like of the raw material to be pulverized. It is normally set within the range from room temperature to the boiling point of the solvent. The extraction time is also not particularly limited and may be appropriately set in accordance with the size, solvent type, extraction temperature, and the like of the raw material to be pulverized. Furthermore, the extraction may be conducted under stirring, allowed to stand without stirring, or ultrasonicated.

For example, the raw materials of the aforementioned plant extracts can be immersed in a solvent and extracted at room temperature or 80° C. to 100° C. The extract liquid obtained by the extraction process is filtered and can be used as an active ingredient, directly or after being concentrated or dried hard, if desired. For this extraction process, shredded or pulverized raw materials may be used. Crude raw materials or dried raw materials may also be used, or roasted raw materials may be used. Roasting methods are not particularly limited, and can include a method for roasting at 80° C. to 120° C. for 0.5 hours to 2 hours.

The type of solvent to be used for extraction is not particularly limited, and water (including hot water etc.), alcohol (for example, methanol, ethanol, 1-propanol, 2-propanol, 1-butanol, 2-butanol), glycol (for example, 1,3-butylene glycol, propylene glycol), glycerin, ketone (for example, acetone, methyl ethyl ketone), ether (for example, diethyl ether, dioxane, tetrahydrofuran, propyl ether), acetonitrile, ester (for example, ethyl acetate, butyl acetate), aliphatic hydrocarbon (for example, hexane, heptane, liquid paraffin), aromatic hydrocarbon (for example, toluene, xylene), halogenated hydrocarbon (for example, chloroform), or a mixed solvent of two or more thereof is preferred.

By such an extracting operation, the effective ingredient is extracted from the raw material, and dissolves in a solvent. The solvent containing the extract may be used directly or may be used after being allowed to stand several days for aging. In addition, it may be used after being subjected to a common purification processing such as sterilization, washing, filtration, decolorization, or deodorization. It may also be used after concentration or dilution as needed. Furthermore, the solid (dried material) resulting after all of the solvent is volatized may be used, or the dried material may be redissolved in any solvent and be used.

Examples of another aspect of applying D-pantothenyl alcohol to the skin include a method for applying it in combination with a skin-whitening compound. Examples of skin-whitening compounds preferably include a 4-alkyl resorcinol, a compound represented by the following general formula (1), a compound represented by the following general formula (2), a compound represented by the following general formula (3), ursolic acid phosphate ester, salts thereof, and the like. It should be noted that, unless otherwise specified, for compounds having optical isomers, any of the L form, the D form, and the racemate (DL form) is intended to be included in the present invention.

A salt, as used herein, refers to one which may be used without particular limitation as long as it is one which is used for skin external preparations. For example, sodium, alkali metal salts such as potassium, alkaline earth metal salts such as calcium and magnesium, ammonium salts, organic amine salts such as triethylamine and triethanolamine, basic amino acid salts such as lysine and arginine, and the like are preferably exemplified. Among these salts, particularly preferred are alkali metals, and among others, sodium salts are particularly preferred.

About 4-alkyl resorcinols, see WO2007/148472. For alkyl groups in 4-alkyl resorcinols, $C_3$-$C_{10}$ alkyl groups are preferable, and among these, $C_3$-$C_6$ alkyl groups are preferable. Specifically, examples can include n-propyl groups, isopropyl groups, n-butyl groups, isobutyl groups, sec-butyl groups, tert-butyl groups, amyl groups, n-hexyl groups, cyclohexyl groups, octyl groups, isooctyl groups, and the like. In the method of the present invention, 4-n-butyl resorcinol in particular is preferably used.

(1)

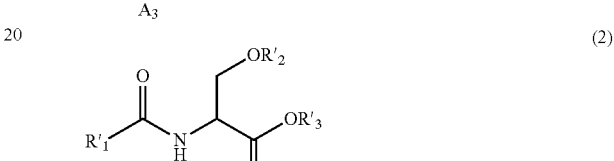

(2)

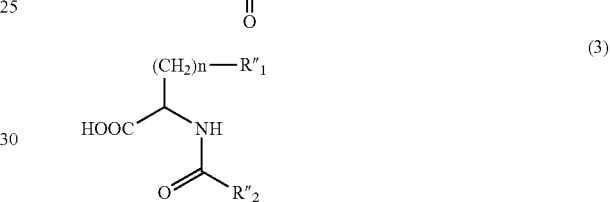

(3)

In the general formula (1), $A_1$, $A_2$, and $A_3$ independently represent a phenyl which optionally contains a substituent. The substituent is selected from hydroxyl, $C_1$-$C_4$ alkyl, and $C_1$-$C_4$ alkyloxy. X is a nitrogen atom or oxygen atom.

In the general formula (1), —X—$R_1$ is represented by the following general formula (4):

(4)

In the general formula (4), $X_1$ is a nitrogen atom. $R_2$ and $R_3$ are bound to each other to form, together with $X_1$, a $C_2$-$C_8$ heterocyclic ring or hydrocarbon ring which optionally has a substituent. Here, the carbon number is defined by an actual carbon number. When the heterocyclic ring or hydrocarbon ring has a substituent, the substituent is preferably selected from a $C_1$-$C_4$ alkyl, $C_1$-$C_4$ alkyloxy, hydroxyl, amino, and oxo. Here, the heterocyclic ring includes any of an aromatic heterocyclic ring, non-aromatic unsaturated heterocyclic ring, and saturated heterocyclic ring. The heterocyclic ring is preferably a saturated heterocyclic ring. In addition, the carbon number of the heterocyclic ring is preferably 3 to 5, more preferably 4 to 5.

The hydrocarbon ring also includes any of an aromatic hydrocarbon ring, non-aromatic unsaturated hydrocarbon ring, and cycloalkyl.

For more detail about a compound of the general formula (1) wherein —X—$R_1$ is represented by the general formula (4), see WO2010/074052. Preferable examples include the following compounds 1 to 12.

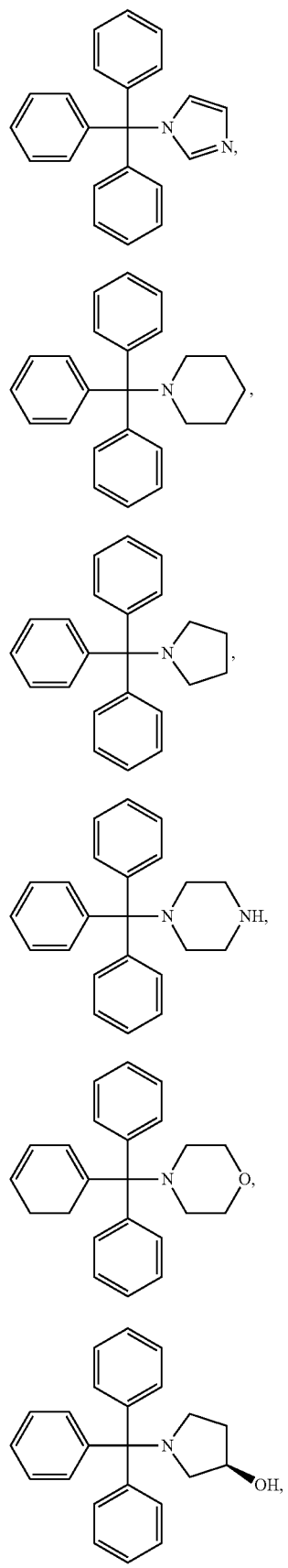
(Compound 1)
(Compound 2)
(Compound 3)
(Compound 4)
(Compound 5)
(Compound 6)
-continued
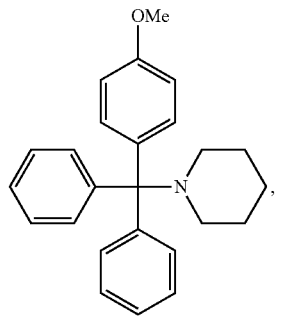
(Compound 7)
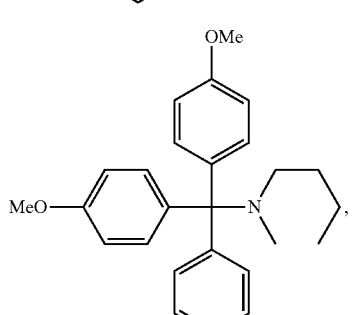
(Compound 8)
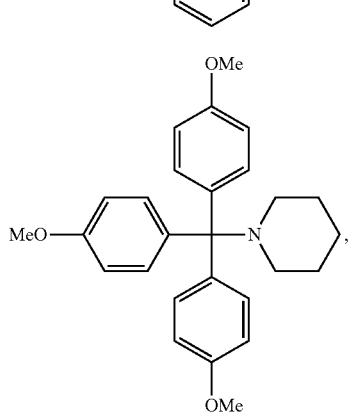
(Compound 9)
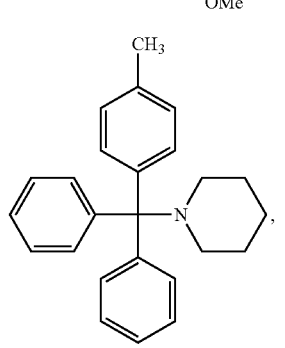
(Compound 10)
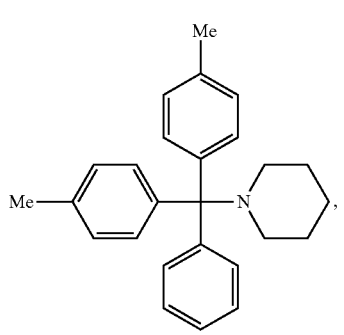
(Compound 11)

(Compound 12)

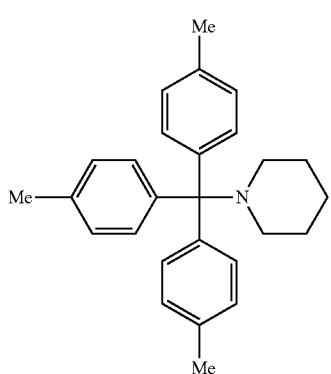

Alternatively, in the general formula (1), —X—R$_1$ is represented by the following general formula (5):

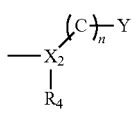

(5)

In the general formula (5), X$_2$ is a nitrogen atom or oxygen atom.

n is an integer of 1 to 5.

n is preferably an integer of 1 to 3.

Y is a hydroxyl group or amino group.

When Y is amino, X$_2$ is preferably an oxygen atom.

In the general formula (5), R$_4$ exists when X$_2$ is a nitrogen atom, and represents a hydrogen atom. R$_4$ does not exist when X$_2$ is an oxygen atom.

For more detail about a compound of the general formula (1) wherein —X—R$_1$ is represented by the general formula (5), see WO2010/074052.

Preferable examples include the following compounds 13 to 22.

(Compound 13)

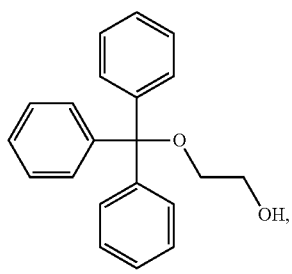

(Compound 14)

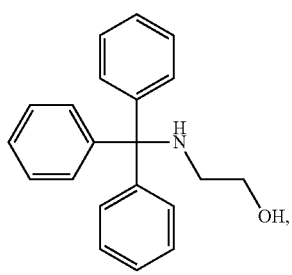

(Compound 15)

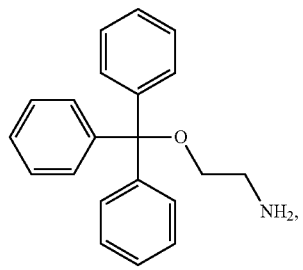

(Compound 16)

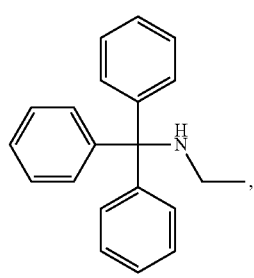

(Compound 17)

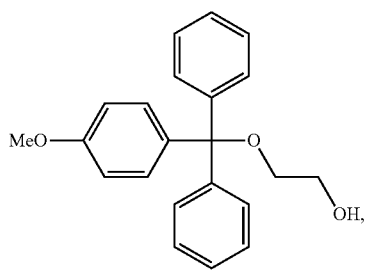

(Compound 18)

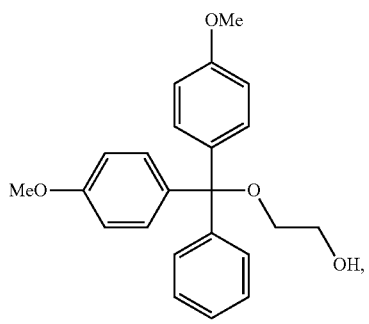

(Compound 19)

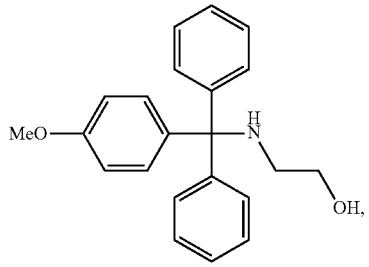

(Compound 20)

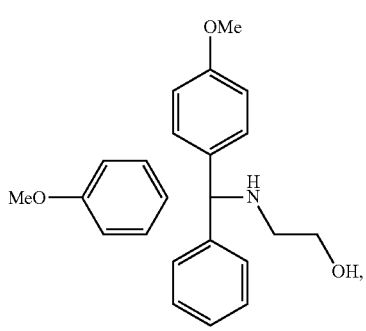

(Compound 21)

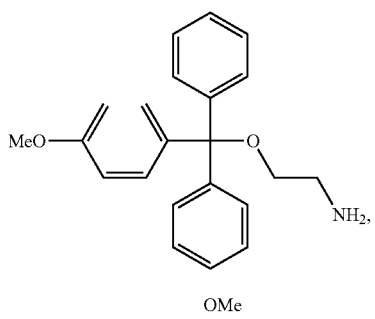

(Compound 22)

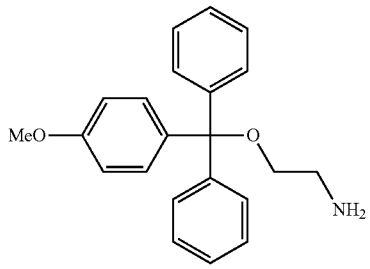

Alternatively, in the general formula (1), —X—$R_1$ is represented by the following general formula (6):

    (6)

In the general formula (6), $X_3$ is an oxygen atom or nitrogen atom.

In the general formula (6), p is the number corresponding to $X_3$.

For more detail about a compound of the general formula (1) wherein —X—$R_1$ is represented by the general formula (6), see WO2010/074052.

Preferable examples include the following compounds 23 to 29.

(Compound 23)

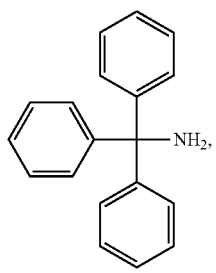

(Compound 24)

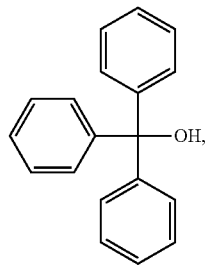

(Compound 25)

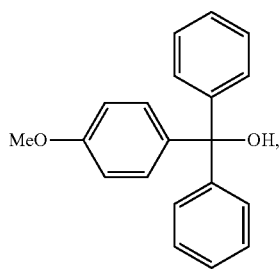

(Compound 26)

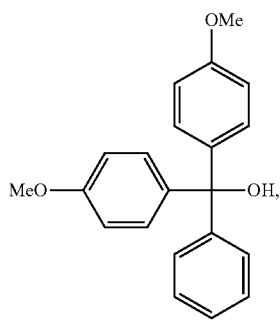

(Compound 27)

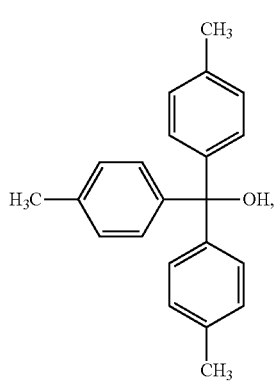

(Compound 28)

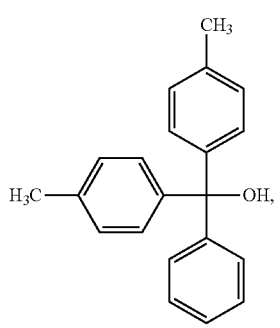

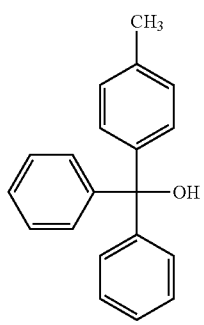
(Compound 29)

In the general formula (2), $R'_1$ represents an aromatic group which is unsubstituted or contains a substituent; the substituent is a $C_1$-$C_4$ linear or branched alkyl group, $C_1$-$C_4$ linear or branched alkoxy group, halogen atom, or $C_1$-$C_4$ halogenated alkyl group; and the aromatic group is a phenyl group, naphthyl group, or biphenyl group.

$R'_2$ represents a hydrogen atom, $C_1$-$C_4$ linear or branched alkyl group, or $C_1$-$C_3$ linear or branched alkyl acyl group.

$R'_3$ represents a hydrogen atom or $C_1$-$C_4$ linear or branched alkyl group.

For more detail about a compound represented by the general formula (2), see WO2011/074643.

Preferable examples include the following compounds 30 to 44.

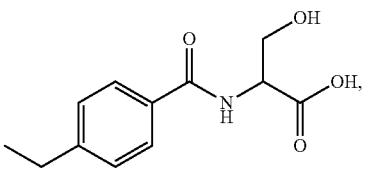
(Compound 30)

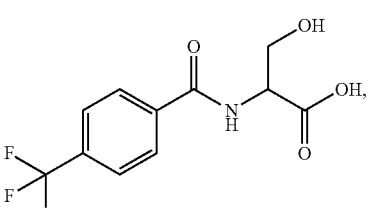
(Compound 31)

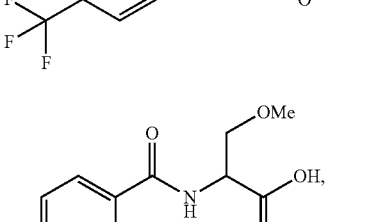
(Compound 32)

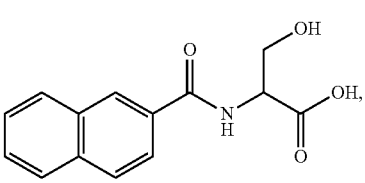
(Compound 33)

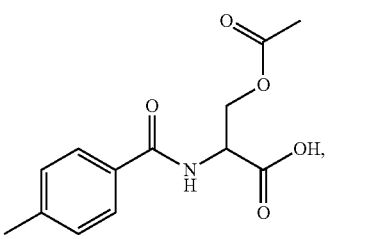
(Compound 34)

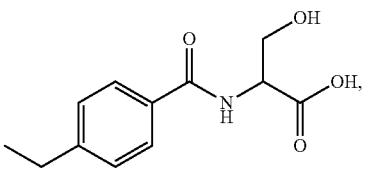
(Compound 35)

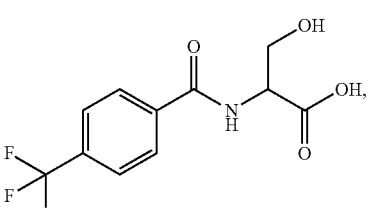
(Compound 36)

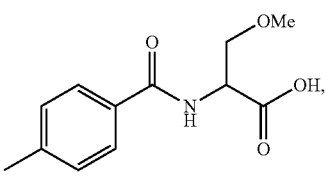
(Compound 37)

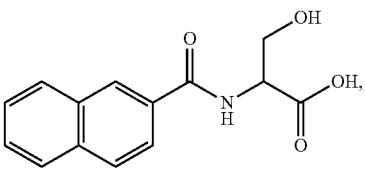
(Compound 38)

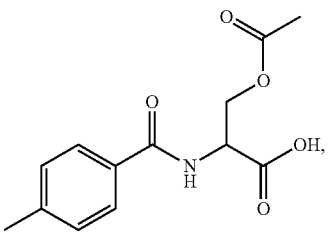
(Compound 39)

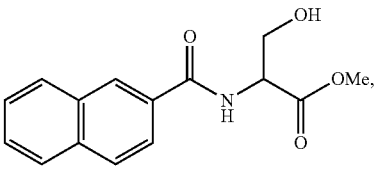
(Compound 40)

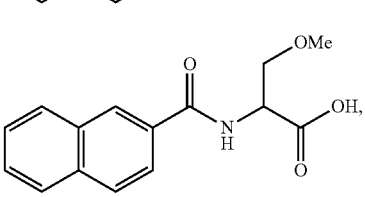
(Compound 41)

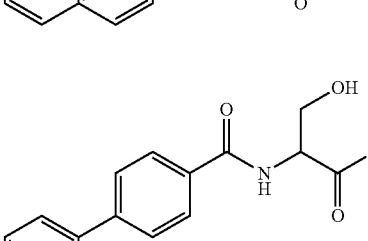
(Compound 42)

-continued (Compound 43)
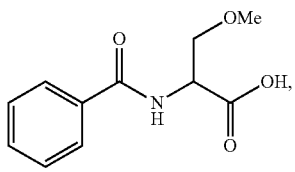

(Compound 44)
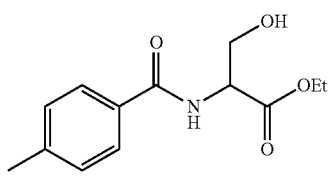

In the general formula (3), $R''_1$ represents —SH, —$SO_3H$, —S—S—$X_1$, —S—$X_2$, —SO—$X_3$, or —$SO_2$—$X_4$, in which $X_1$ to $X_4$ are independently a hydrogen atom or $C_1$-$C_8$ aliphatic hydrocarbon group. $R''_2$ represents a $C_5$-$C_{12}$ aromatic group which may be unsubstituted or optionally contains a substituent, and the aromatic group is preferably a phenyl group. n represents an integer of 1 or 2. The substituent is preferably a $C_1$-$C_4$ alkyl group, $C_1$-$C_4$ alkoxy group, or phenyl group.

For more detail about a compound represented by the general formula (3), see WO2010/058730.

Preferable examples include the following compounds 45 to 52.

(Compound 45)
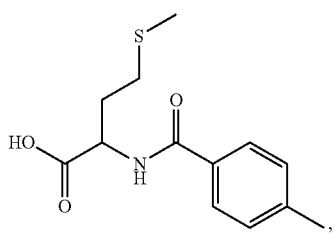

(Compound 46)
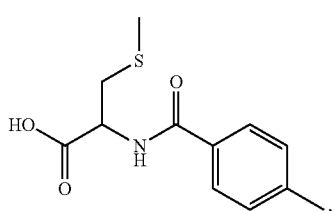

(Compound 47)
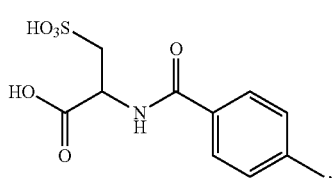

(Compound 48)
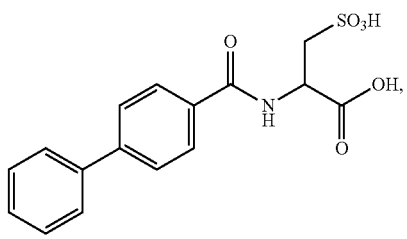

(Compound 49)
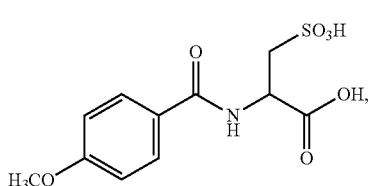

(Compound 50)
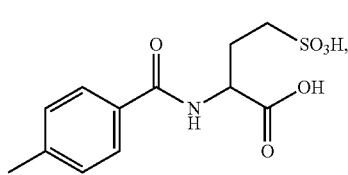

(Compound 51)
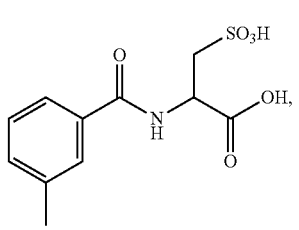

(Compound 52)
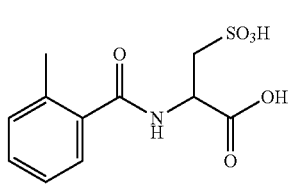

An ursolic acid phosphate ester is represented by the following formula. For more detail, see WO2006/132033.

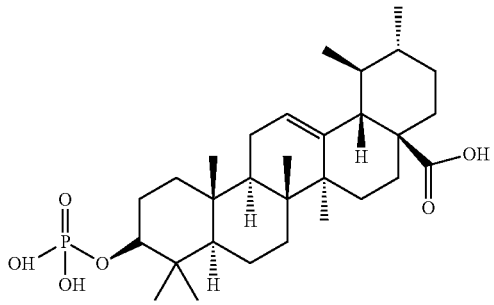

When a 4-alkyl resorcinol, a compound represented by the general formula (1), (2), or (3), or a salt thereof is formulated into a skin external preparation for the purpose of a skin-whitening effect, among a 4-alkyl resorcinol, a compound represented by the general formula (1), (2), or (3), an ursolic acid phosphate ester, and salts thereof, one species alone may be contained or two or more species may be contained.

The content of a 4-alkyl resorcinol, or a compound represented by the general formula (1), (2), or (3), or a salt thereof in a skin external preparation is preferably 0.001 to 10% by mass, more preferably 0.01 to 5% by mass, still more preferably 0.1 to 3% by mass, relative to the total amount of the skin external preparation.

A method in which a 4-alkyl resorcinol, a compound represented by the general formula (1), (2), or (3), an ursolic acid phosphate ester, or a salt thereof is applied in combination with D-pantothenyl alcohol to the skin for the purpose of a skin-whitening effect follows the aforementioned case where a plant extract having a melanogenesis inhibitory action and D-pantothenyl alcohol are applied to the skin.

Experiment 3: Confirmation of Synergistic Effect Based on Combination of Either Plant Extract Having Melanogenesis Inhibitory Action or Existing Skin-Whitening Compound and D-Pantothenyl Alcohol In order to confirm the synergistic effect based on combining D-pantothenyl alcohol and the aforementioned plant extract having a melanogenesis inhibitory action and in order to confirm the synergistic effect based on combining D-pantothenyl alcohol and a skin-whitening compound, the experiment was conducted in the same manner as in the aforementioned <Experiment 1: Melanogenesis Inhibition Experiment> and <Experiment 2: Keratinocyte Cell Proliferation Experiment>. While 0 mM or 0 μM D-pantothenyl alcohol was used as a control similarly, the 1 mM D-pantothenyl alcohol in <Experiment 1> was replaced with each of the following samples (1) to (3) for experimenting.

Sample (1): 1 mM D-pantothenyl alcohol
Sample (2): one 1% species selected from the plant extracts listed Table 1 (extracts 1 to 50), or one 0.1 μg/mL species selected from existing skin-whitening compounds
Sample (3): a combination of the sample (1) and each of the samples (2)

In addition, the 15 μM and the 150 μM D-pantothenyl alcohol in <Experiment 2> were replaced with the aforementioned samples (1) to (3) respectively for experimenting. The results are shown in Table 2. Note that the amount of melanin (%) and the cell proliferation rate (%) in Table 2 are both a ratio to the control, as described in Experiment 1 and Experiment 2.

As a note, the existing skin-whitening compounds used here are "4-n-butyl resorcinol", "ursolic acid phosphate ester", the aforementioned compounds 1, 31, and 45.

In the present experiment, as the compound 1, 1-(triphenylmethyl) imidazole was synthesized by the method described in WO2010/074052 and was used. As the compound 31, N-benzoyl-L-serine was synthesized by the method described in WO2011/074643 and was used. As the compound 45, N-(toluyl) methionine was made by the method described in WO2010/058730 and was used. The below-mentioned <Skin-whitening Rate> is as above.

TABLE 1

| No. | Plant Extracts |
|---|---|
| 1 | *Uncaria gambir* extract |
| 2 | *Isodon japonicus* extract |
| 3 | *Echinacea angustifolia* leaf extract |
| 4 | *Lithospermum erythrorhizon* root extract |
| 5 | *Carthamus tinctorius* flower extract |
| 6 | *Persea gratissima* fruit extract |
| 7 | *Abelmoschus esclentus* fruit extract |

TABLE 1-continued

| No. | Plant Extracts |
|---|---|
| 8 | *Actinidia chinensis* fruit extract |
| 9 | *Alpinia speciosa* leaf extract |
| 10 | *Saponaria officinalis* extract |
| 11 | Caprifoliaceae extract |
| 12 | green tea extract |
| 13 | *Benincasa cerifera* seed exract |
| 14 | *Allium sativum* extract |
| 15 | *Citrus aurantifolia* fruit juice extract |
| 16 | natto extract |
| 17 | *Citrus aurantium dulsis* fruit extract |
| 18 | *Valeriana officinalis* extract |
| 19 | *Cucumis sativus* extract |
| 20 | *Prunus armeniaca* extract |
| 21 | *Gardenia florida* extract |
| 22 | *Citrus grandis* fruit extract |
| 23 | *Arctium lappa* root extract |
| 24 | black tea extract |
| 25 | *Equisetum arvense* extract |
| 26 | *Malva sylvestris* extract |
| 27 | *Jujube* extract |
| 28 | *Solanum lycopersicum* extract |
| 29 | *Daucus carota sativa* extract |
| 30 | Hoelen extract |
| 31 | *Lilium candidum* bulb extract |
| 32 | *Litchi chinensis* extract |
| 33 | *Lactuca scariola sativa* leaf extract |
| 34 | *Citrus medica limonum* fruit extract |
| 35 | royal jelly extract |
| 36 | *Pleurotus cornucopiae* extract |
| 37 | Algae extract |
| 38 | *Zanthoxylum bungeanum* pericarp extract |
| 39 | *Coprinus comatus* extract |
| 40 | *Salix alba* bark extract |
| 41 | horsetail extract |
| 42 | *Ampelopsis grossedentata* leaf extract |
| 43 | *Acer palmatum* leaf extract |
| 44 | *Opuntia streptacantha* stem extract |
| 45 | *Bidens pilosa* extract |
| 46 | *Prunus mume* fruit water extract |
| 47 | *Mallotus philippinensis* bark extract |
| 48 | *Salacia reticulata* wood extract |
| 49 | *Euphrasia officinalis* extract |
| 50 | *Nelumbo nucifera* germ extract |

TABLE 2

| | Melanin Amount (%) | | | Cell Proliferation Rate (%) | | |
|---|---|---|---|---|---|---|
| | Sample (1) | Sample (2) | Sample (3) | Sample (1) | Sample (2) | Sample (3) |
| Plant extract 1 | 69.8 | 96.2 | 61.2 | 123.3 | 103.2 | 136.3 |
| Plant extract 2 | 69.8 | 95.8 | 62.1 | 123.3 | 96.5 | 130.6 |
| Plant extract 3 | 69.8 | 96.8 | 60.2 | 123.3 | 106.3 | 126.2 |
| Plant extract 4 | 69.8 | 98.6 | 60.8 | 123.3 | 102.3 | 128.6 |
| Plant extract 5 | 69.8 | 97.2 | 61.1 | 123.3 | 101.2 | 130.1 |
| Plant extract 6 | 69.8 | 99.4 | 65.3 | 123.3 | 118.9 | 129.3 |
| Plant extract 7 | 69.8 | 98.3 | 64.3 | 123.3 | 109.5 | 128.1 |
| Plant extract 8 | 69.8 | 97.9 | 63.8 | 123.3 | 103.5 | 130.3 |
| Plant extract 9 | 69.8 | 98.6 | 63.5 | 123.3 | 91.2 | 143.8 |
| Plant extract 10 | 69.8 | 99.4 | 65.4 | 123.3 | 114.5 | 128.4 |
| Plant extract 11 | 69.8 | 98.6 | 64.4 | 123.3 | 105.7 | 130.6 |
| Plant extract 12 | 69.8 | 98.3 | 64.6 | 123.3 | 122.1 | 166.2 |

TABLE 2-continued

| | Melanin Amount (%) | | | Cell Proliferation Rate (%) | | |
|---|---|---|---|---|---|---|
| | Sample (1) | Sample (2) | Sample (3) | Sample (1) | Sample (2) | Sample (3) |
| Plant extract 13 | 69.8 | 99.5 | 65.3 | 123.3 | 117.0 | 137.9 |
| Plant extract 14 | 69.8 | 97.7 | 63.4 | 123.3 | 106.0 | 128.4 |
| Plant extract 15 | 69.8 | 98.4 | 64.3 | 123.3 | 98.4 | 136.3 |
| Plant extract 16 | 69.8 | 98.9 | 65.1 | 123.3 | 106.0 | 142.0 |
| Plant extract 17 | 69.8 | 97.8 | 64.1 | 123.3 | 109.5 | 128.4 |
| Plant extract 18 | 69.8 | 97.7 | 64.0 | 123.3 | 93.5 | 130.3 |
| Plant extract 19 | 69.8 | 99.3 | 65.5 | 123.3 | 112.2 | 129.6 |
| Plant extract 20 | 69.8 | 98.2 | 64.1 | 123.3 | 115.9 | 130.0 |
| Plant extract 21 | 69.8 | 98.6 | 64.7 | 123.3 | 111.3 | 133.0 |
| Plant extract 22 | 69.8 | 99.4 | 65.4 | 123.3 | 112.2 | 131.9 |
| Plant extract 23 | 69.8 | 98.3 | 64.0 | 123.3 | 93.1 | 128.9 |
| Plant extract 24 | 69.8 | 97.8 | 63.7 | 123.3 | 94.7 | 130.9 |
| Plant extract 25 | 69.8 | 98.5 | 64.6 | 123.3 | 114.1 | 132.1 |
| Plant extract 26 | 69.8 | 99.1 | 65.0 | 123.3 | 117.3 | 131.4 |
| Plant extract 27 | 69.8 | 99.0 | 64.8 | 123.3 | 114.8 | 136.5 |
| Plant extract 28 | 69.8 | 98.7 | 64.6 | 123.3 | 115.0 | 128.6 |
| Plant extract 29 | 69.8 | 98.3 | 64.3 | 123.3 | 112.2 | 129.6 |
| Plant extract 30 | 69.8 | 99.2 | 65.0 | 123.3 | 119.2 | 134.9 |
| Plant extract 31 | 69.8 | 97.6 | 63.6 | 123.3 | 106.5 | 137.2 |
| Plant extract 32 | 69.8 | 98.6 | 64.5 | 123.3 | 120.8 | 143.9 |
| Plant extract 33 | 69.8 | 98.8 | 64.6 | 123.3 | 104.8 | 132.8 |
| Plant extract 34 | 69.8 | 99.8 | 65.8 | 123.3 | 116.4 | 136.0 |
| Plant extract 35 | 69.8 | 98.6 | 64.9 | 123.3 | 117.8 | 137.2 |
| Plant extract 36 | 69.8 | 99.8 | 69.7 | 123.3 | 101.5 | 129.8 |
| Plant extract 37 | 69.8 | 97.6 | 69.7 | 123.3 | 102.4 | 129.9 |
| Plant extract 38 | 69.8 | 99.1 | 69.4 | 123.3 | 102.8 | 130.1 |
| Plant extract 39 | 69.8 | 99.5 | 69.6 | 123.3 | 102.3 | 129.8 |
| Plant extract 40 | 69.8 | 98.7 | 69.7 | 123.3 | 100.2 | 130.3 |
| Plant extract 41 | 69.8 | 98.8 | 65.0 | 123.3 | 101.3 | 123.2 |
| Plant extract 42 | 69.8 | 98.3 | 64.3 | 123.3 | 102.3 | 123.1 |
| Plant extract 43 | 69.8 | 98.6 | 64.8 | 123.3 | 105.3 | 123.3 |
| Plant extract 44 | 69.8 | 98.9 | 64.1 | 123.3 | 100.8 | 122.9 |
| Plant extract 45 | 69.8 | 98.8 | 64.5 | 123.3 | 99.9 | 123.5 |
| Plant extract 46 | 69.8 | 99.8 | 69.9 | 123.3 | 99.8 | 123.3 |
| Plant extract 47 | 69.8 | 98.6 | 69.8 | 123.3 | 100.9 | 123.4 |
| Plant extract 48 | 69.8 | 99.1 | 69.8 | 123.3 | 101.6 | 123.3 |
| Plant extract 49 | 69.8 | 98.6 | 69.7 | 123.3 | 102.7 | 123.0 |
| Plant extract 50 | 69.8 | 99.3 | 69.8 | 123.3 | 100.6 | 123.1 |
| 4-n-butyl resorcinol | 69.8 | 93.2 | 59.4 | 123.3 | 120.3 | 140.7 |
| Ursolic acid phosphate ester | 69.8 | 98.4 | 61.0 | 123.3 | 118.6 | 139.8 |
| Compound 1 | 69.8 | 93.1 | 59.1 | 123.3 | 112.1 | 139.7 |
| Compound 31 | 69.8 | 94.6 | 60.1 | 123.3 | 118.7 | 139.8 |
| Compound 45 | 69.8 | 93.4 | 59.8 | 123.3 | 113.2 | 140.2 |

It is recognized from the above results that the synergistic effect of a melanogenesis inhibitory action and a keratinocyte cell proliferation action is obtained by applying the plant extracts 1 to 35, the compounds 1, 31, or 45, 4-n-butyl resorcinol, or an ursolic acid phosphate ester, in combination with D-pantothenyl alcohol. It is also recognized that the synergistic effect of a keratinocyte cell proliferation action is obtained by applying D-pantothenyl alcohol and the plant extracts 36 to 40 in combination and that the synergistic effect of a melanogenesis inhibition is obtained by applying D-pantothenyl alcohol and the plant extracts 41 to 45 in combination.

Above all, when the synergistic effect is achieved for a melanogenesis inhibitory action and a keratinocyte cell proliferation action, it is considered that the turnover promoting function, i.e., the melanin discharge promoting function, of D-pantothenyl alcohol was able to be further enhanced, and the skin-whitening rate for pigmented skin can be expected to be further accelerated.

In the preparation of skin-whitening cosmetics with D-pantothenyl alcohol formulated thereinto, the cosmetics can contain an ingredient used in ordinary cosmetics. In addition, their dosage forms are not limited in any way. Below, ingredients which can be contained in skin-whitening cosmetics when applied to skin-whitening cosmetics will be described.

Examples of effective ingredients include skin-whitening ingredients other than D-pantothenyl alcohol, anti-wrinkle ingredients, anti-inflammatory ingredients other than pantothenyl alcohol, and extracts derived from plants and animals, and the like. When D-pantothenyl alcohol is used as an effective ingredient, two or more effective ingredients may be contained.

The skin-whitening ingredients are not particularly limited as long as they are generally used for cosmetics. Examples include 4-n-butyl resorcinol, ascorbic acid glucoside, 3-O-ethyl ascorbic acid, tranexamic acid, arbutin, 1-triphenylmethylpiperidine, 1-triphenylmethylpyrrolidine, 2-(triphenylmethyloxy)ethanol, 2-(triphenylmethylamino) ethanol, 2-(triphenylmethyloxy)ethylamine, triphenylmethylamine, triphenylmethanol, triphenylmethane, and aminodiphenylmethane, N-(p-toluyl)cysteic acid, N-(p-methoxybenzoyl)cysteic acid, and the like. Still other skin-whitening ingredients include N-benzoyl-serine, N-(p-methylbenzoyl)serine, N-(p-ethylbenzoyl)serine, N-(p-methoxybenzoyl)serine, N-(p-fluorobenzoyl)serine, N-(p-trifluoromethylbenzoyl)serine, N-(2-naphthoyl)serine, N-(4-phenylbenzoyl)serine, N-(p-methylbenzoyl)serine methyl ester, N-(p-methylbenzoyl)serine ethyl ester, N-(2-naphthoyl) serine methyl ester, N-benzoyl-O-methylserine, N-(p- methylbenzoyl)-O-methylserine, N-(p-methylbenzoyl)-O-acetyl serine, N-(2-naphthoyl)-O-methylserine, and the like.

These skin-whitening ingredients can be already commercially available or can also be obtained synthetically.

The content of skin-whitening ingredients in skin-whitening cosmetics is usually 0.01 to 30% by mass, preferably 0.1 to 10% by mass, more preferably 1 to 5% by mass.

The anti-wrinkle ingredients are not particularly limited as long as they are generally used for cosmetics. Examples include vitamin A or a derivative thereof, retinol, retinal, retinoic acid, tretinoin, isotretinoin, tocopherol retinoate, retinol palmitate, retinol acetate, benzyl ursolate ester, ursolic acid phosphate ester, benzyl betulinate ester, and benzilic acid phosphate ester. The content of the anti-wrinkle ingredients in cosmetics is usually 0.01 to 30% by mass, preferably 0.1 to 10% by mass, more preferably 1 to 5% by mass.

The extracts derived from plants and animals are not particularly limited as long as they are generally used for pharmaceuticals, cosmetics, food, and the like. Examples of preferable extracts include *Akebia quinata* extract, *Thujopsis dolabrata* branch extract, *Asparagus officinalis* extract, *Persea gratissima* fruit extract, *Hydrangea serrata* leaf extract, *Prunus amygdalus dulcis* seed extract, *Arnica* extract, *Aloe* extract, *Aronia* extract, *Prunus armeniaca* extract, *Ginkgo biloba* extract, *Indian kino* extract, *Foeniculum vulgare* fruit extract, *Aralia cordata* extract, *Rosa multiflora* fruit extract, *Acanthopanax senticosus* extract, *Isodonis japonicus* extract, *Scutellaria* root extract, *Phellodendron amurense* extract, *Coptis* extract, *Panax ginseng* extract, *Hypericum erectum* extract, *Lamium album* extract, *Citrus aurantium dulsis* fruit extract, *Pyracantha fortuneana* extract, *Pueraria lobata* root extract, *Chamomilla* extract, *Daucus carota sativa* extract, *Artemisia capillaris* extract, *Hemerocallis fulva* extract, *Actinidia chinensis* fruit extract, *Cucumis sativus* extract, *Psidium guajava* extract, *Sophora* root extract, *Gardenia florida* extract, *Sasa veitchii* leaf extract, *Sophora flavescens* extract, *Juglans* extract, *Citrus grandis* fruit extract, black rice extract, *Chlorella vulgaris* extract, *Morus alba* extract, *Mucuna birdwoodiana* stem extract, *Alpinia speciosa* leaf extract, *Gentiana lutea* extract, *Geranium thunbergii* extract, black tea extract, *Arctium lappa* root extract, *Oryza sativa* extract, Rice ferment extract, Rice bran ferment extract, *Oryza sativa* germ oil, *Vaccinium vitis-idaea* extract, *Salvia sclarea* extract, *Saponaria officinalis* extract, *Sasa* extract, *Crataegus cuneata* fruit extract, *Coriandrum sativum* fruit extract, *Zanthoxylum piperitum* extract, *Lentinus edodes* extract, *Rehmannia* root extract, *Lithospermum erythrorhizon* root extract, *Perilla* extract, *Tilia japonica* extract, *Spiraea ulmaria* flower extract, *Paeonia albiflora* extract, *Zingiber officinale* root extract, *Acorus calamus* root extract, *Betula alba* extract, *Equisetum arvense* extract, *Stevia rebaudiana* extract, *Stevia* fermented product, *Hedera helix* extract, *Crataegus oxyacantha* extract, *Sambucus nigra* extract, *Achillea milefolium* extract, *Mentha piperita* extract, *Salvia officinalis* extract, *Malva sylvestris* extract, *Cnidium officinale* extract, *Swertia japonica* extract, *Morus alba* root extract, *Rheum* extract, *Glycine soja* extract, *Jujube* extract, *Thymus vulgaris* extract, *Taraxacum* extract, tea extract, *Eugenia caryophyllus* flower extract, *Rutaceae* extract, sweet tea extract, *Capsicum annuum* extract, *Angelica acutiloba* extract, *Calendula officinalis* extract, *Prunus persica* extract, *Citrus aurantium* extract, *Houttuynia cordata* extract, *Solanum lycopersicum* extract, natto extract, *Daucus carota sativa* extract, *Allium sativum* extract, *Rosa canina* fruit extract, *Hibiscus sabdariffa* flower extract, *Ophiopogon japonicus* extract, *Nelumbo nucifera* extract, *Carum petroselinum* extract, birch extract, *Hamamelis virginiana* extract, *Isodon japonicus* extract, *Cupressaceae* extract, *Eriobotrya japonica* extract, *Tussilago farfara* extract, butterbur sprout extract, *Hoelen* extract, *Ruscus aculeatus* root extract, *Vitis vinifera* fruit extract, *Vitis vinifera* seed extract, *Luffa cylindrica* extract, *Carthamus tinctorius* flower extract, *Mentha piperita* extract, *Tilia platyphyllos* flower extract, *Paeonia suffruticosa* root extract, *Humulus lupulus* extract, *Pinus sylvestris* cone extract, *Origanum majorana* leaf extract, *Aesculus hippocastanum* extract, *Lysichiton* extract, *Sapindus mukorossi* peel extract, *Melissa officinalis* extract, *Spermatochnaceae* extract, *Prunus persica* extract, *Centaurea cyanus* flower extract, *Eucalyptus globulus* extract, *Saxifraga sarmentosa* extract, *Citrus junos* fruit extract, *Lilium candidum* bulb extract, coix seed extract, *Artemisia* extract, *Lavandula angustifolia* extract, green tea extract, *Pyrus malus* fruit extract, rooibos tea extract, *Litchi chinensis* extract, *Lactuca scariola sativa* leaf extract, *Citrus medica* limonum fruit extract, *Forsythia* extract, *Astragalus sinicus* extract, rose extract, *Rosmarinus officinalis* extract, *Anthemis nobilis* flower extract, royal jelly extract, and *Sanguisorba officinalis* root extract.

The content of the extracts derived from plants and animals in cosmetics is usually 0.01 to 30% by mass, preferably 0.1 to 10% by mass, more preferably 1 to 5% by mass.

Examples of anti-inflammatory ingredients include Kurarinone, glabridin, glycyrrhizic acid and glycyrrhetinic acid and the like, and are preferably, glycyrrhizic acid and a salt thereof, glycyrrhetinic acid alkyl and a salt thereof, as well as glycyrrhetinic acid and a salt thereof.

The content of the anti-inflammatory ingredients in cosmetics is usually 0.01 to 30% by mass, preferably 0.1 to 10% by mass, more preferably 1 to 5% by mass.

Examples of oily ingredients include polar oils, volatile hydrocarbon oils, and the like.

Examples of polar oils include, as synthetic ester oils, isopropyl myristate, cetyl octanoate, octyldodecyl myristate, isopropyl palmitate, butyl stearate, hexyl laurate, myristyl myristate, decyl oleate, hexyl decyl dimethyl-octanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprate, diisostearyl malate, glycerin di-2-heptylundecanoate, trimethylol propane tri-2-ethylhexylate, trimethylolpropane triisostearate, pentane erythritol tetra-2-ethylhexylate, glycerin tri-2-ethylhexylate, and trimethylolpropane triisostearate.

Additional examples include cetyl 2-ethylhexanoate, 2-ethylhexyl palmitate, glycerin trimyristate, glyceride tri-2-heptylundecanoate, castor oil fatty acid methyl ester, oil oleate, cetostearyl alcohol, acetone glyceride, 2-heptylundecyl palmitate, diisobutyl adipate, 2-octyldodecyl N-lauroyl-L-glutamate ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, triethyl citrate, octyl methoxycinnamate, and the like.

Examples of natural oils include avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, Chinese tung oil, Japanese tung oil, jojoba oil, germ oil, triglycerol, glycerin trioctanoate, glycerin triisopalmitate, and the like.

Examples of volatile hydrocarbon oils include isododecane, isohexadecane, and the like.

Examples of surfactants include anionic surfactants such as fatty acid soap (sodium laurate, sodium palmitate, etc.), potassium laurylsulfate, and triethanolamine alkylsulfate ether, and cationic surfactants such as stearyl trimethyl ammonium chloride, benzalkonium chloride, and lauryl amine oxide;

amphoteric surfactants such as betaine-based surfactants (alkyl betaine, amido betaine, sulfobetaine, etc.), imidazoline-based amphoteric surfactants (2-cocoyl-2-imidazolinium hydroxide-1-carboxyethyloxy disodium salt etc.), and acyl methyl taurine; and non-ionic surfactants such as sorbitan fatty acid esters (sorbitan monostearate, sorbitan sesquioleate, etc.), glycerin fatty acids (glycerin monostearate etc.), propylene glycol fatty acid esters (propylene glycol monostearate etc.), hydrogenated castor oil derivatives, glycerin alkyl ethers, POE sorbitan fatty acid esters (POE sorbitan monooleate, polyoxyethylene sorbitan monostearate, etc.), POE sorbitol fatty acid esters (POE-sorbit monolaurate etc.), POE glycerine fatty acid esters (POE-glycerine monoisostearate, etc.), POE fatty acid esters (polyethylene glycol monooleate, POE distearate, etc.), POE alkyl ethers (POE2-octyldodecyl ether etc.), POE alkylphenyl ethers (POE nonylphenyl ether etc.), Pluronic type ethers, POE/POP alkyl ethers (POE/POP2-decyltetradecyl ether etc.), Tetronic ethers, POE castor oil/hydrogenated castor oil derivatives (POE castor oil, POE hydrogenated castor oil, etc.), sucrose fatty acid esters, and alkyl glucosides Examples of polyhydric alcohols include polyethylene glycol, glycerine, 1,3-butylene glycol, erythritol, sorbitol, xylitol, maltitol, propylene glycol, dipropylene glycol, diglycerine, isoprene glycol, 1,2-pentanediol, 2,4-hexylene glycol, 1,2-hexanediol, 1,2-octanediol, and the like.

Examples of thickeners include guar gum, quince seed, carrageenan, galactan, gum arabic, pectin, mannan, starch, xanthan gum, curdlan, methyl cellulose, hydroxyethyl cellulose, carboxymethyl cellulose, methyl hydroxypropyl cellulose, chondroitin sulfate, dermatan sulfate, glycogen, sodium heparan sulfate, hyaluronic acid, sodium hyaluronate, tragacanth, keratan sulfate, chondroitin, mucoitin sulfate, hydroxyethyl guar gum, carboxymethyl guar gum, dextran, keratosulfate sulfate, locust bean gum, succinoglucan, charonic acid, chitin, chitosan, carboxymethyl chitin, agar, polyvinyl alcohol, polyvinyl pyrrolidone, carboxyvinyl polymers, alkyl-modified carboxyvinyl polymers, sodium polyacrylate, polyethylene glycol, and bentonite.

Examples of powders include powder which may be surface-treated, such as mica, talc, kaolin, synthetic mica, calcium carbonate, magnesium carbonate, silicic anhydride (silica), aluminum oxide, and barium sulfate; inorganic pigments which may be surface-treated, such as red iron oxide, yellow iron oxide, black iron oxide, cobalt oxide, ultramarine, iron blue, titanium oxide, and zinc oxide; pearl agents which may be surface-treated such as mica titanium, fish scale guanine, and bismuth oxychloride; organic dyes which may be laked, such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204; and organic powders such as polyethylene powder, methyl polymethacrylate, nylon powder, and organopolysiloxane elastomer.

Examples of ultraviolet absorbers include para-aminobenzoic acid-based ultraviolet absorbers, anthranilic acid-based ultraviolet absorbers, salicylic acid-based ultraviolet absorbers, cinnamic acid-based ultraviolet absorbers, benzophenone ultraviolet absorbers, sugar-based ultraviolet absorbers, and ultraviolet absorbers such as 2-(2'-hydroxy-5'-t-octylphenyl)benzotriazole and 4-methoxy-4'-t-butyldibenzoyl methane.

Skin-whitening cosmetics, without a manufacturing method therefor being particularly limited, can be manufactured using a known method as appropriate, in accordance with the dosage form to be applied of skin-whitening cosmetics. The dosage form, as applied as a skin-whitening cosmetic, can take any of a lotion dosage form, emulsion dosage form, essence dosage form, cream dosage form, and powder-containing dosage form which are normally known.

EXAMPLES

Below, the present invention will be described in further detail with reference to specific experimental examples, but the present invention is not limited to the following aspects only.

Examples 1 to 4

The skin-whitening cosmetics 1 to 4 formulated as shown in the following Tables 3 to 6 were prepared.

TABLE 3

Example 1 (lotion)

| | | (parts by mass) |
|---|---|---|
| (A) | D-pantothenyl alcohol | 1.0 |
| | glycerin | 5.0 |
| | propylene glycol | 4.0 |
| | *Artemisia* extract | 0.1 |
| | *Origanum majorana* leaf extract | 0.1 |
| | purified water | balance |
| (B) | POE(20) sorbitan monolaurate ester | 1.5 |
| | POE(20) lauryl ether | 0.5 |
| | ethanol | 10.0 |
| | perfume | 0.1 |
| | Total | 100.0 |

(Preparation Method) The ingredients of (A) were combined and dissolved at room temperature. The ingredients of (B) were also dissolved at room temperature, added to the formulation (A), and solubilized, to obtain the skin-whitening cosmetic 1.

TABLE 4

Example 2 (emulsion)

| | | (parts by mass) |
|---|---|---|
| (A) | POE(20) hydrogenated castor oil | 1.5 |
| | coconut oil fatty acid monoglyceride | 1.0 |
| | oleic acid triglyceride | 7.5 |
| (B) | D-pantothenyl alcohol | 1.0 |
| | glycerin | 2.5 |
| | *Artemisia* extract | 0.1 |

TABLE 4-continued

Example 2 (emulsion)

| | | (parts by mass) |
|---|---|---|
| | Origanum majorana leaf extract | 0.1 |
| | purified water | balance |
| (C) | perfume | 0.2 |
| | Total | 100.0 |

(Preparation Method) The ingredients of (A) were combined and mixed/heated to 70° C. The ingredients of (B) were combined and mixed/heated to 70° C., the formulation (A) was added thereto and emulsified, and (C) was added under cooling, to obtain the skin-whitening cosmetic 2.

TABLE 5

Example 3 (hand cream)

| | | (parts by mass) |
|---|---|---|
| (A) | petrolatum | 18.0 |
| | cetanol | 8.0 |
| | POE(20) oleyl ether | 1.4 |
| | sorbitan monostearate | 0.8 |
| (B) | D-pantothenyl alcohol | 1.0 |
| | preservative | 0.3 |
| | Artemisia extract | 0.1 |
| | Origanum majorana leaf extract | 0.1 |
| | purified water | balance |
| (C) | perfume | 0.2 |
| | Total | 100.0 |

(Preparation Method) The skin-whitening cosmetic 3 was obtained in the same manner as in Example 2.

TABLE 6

Example 4 (cream)

| | | (parts by mass) |
|---|---|---|
| (A) | POE(30) cetyl ether | 2.0 |
| | glycerin monostearate | 10.0 |
| | liquid paraffin | 10.0 |
| | petrolatum | 4.0 |
| | cetanol | 5.0 |
| | preservative | 0.2 |
| (B) | D-pantothenyl alcohol | 1.0 |
| | propylene glycol | 10.0 |
| | Artemisia extract | 0.1 |
| | Origanum majorana leaf extract | 0.1 |
| | purified water | balance |
| | Total | 100.0 |

(Preparation Method) The ingredients of (A) were combined and heated to 80° C. The ingredients of (B) were combined and heated to 80° C. The mixture of (B) was added to the mixture of (A) under stirring, emulsified under stirring, and then cooled, to obtain the skin-whitening cosmetic 4.

<Evaluation of Skin-Whitening>

The comparative cosmetics 1 to 3 were made in the same manner as the method described in Example 1 except that the "D-pantothenyl alcohol" in Example 1 was replaced with "water", replaced with an existing skin-whitening ingredient, "2-hydroxy-2'-hydroxy-5,5'-dipropyl-1,1'-biphenyl", having a formulation concentration of 1%, and replaced with "disodium adenosine monophosphate" having a formulation concentration of 2%, for the comparative cosmetics 1 to 3 respectively. The skin-whitening cosmetic 1 and the comparative cosmetics 1 to 3 were evaluated for pigmentation inhibitory action in accordance with the following procedure.

A total of four 1.5 cm×1.5 cm sites were provided inside an upper arm of a panelist who voluntarily participated. The provided sites were subjected to a minimal erythema dose (1MED) of ultraviolet irradiation once a day, three times for three consecutive days. The skin-whitening cosmetic 1 and the comparative cosmetics 1 to 3 were applied at 50 μL twice a day for 21 consecutive days after completion of the ultraviolet irradiation in Experiment Day 1 (after completion of the first irradiation). Twenty-four hours after completion of the application in Day 21, each test site was measured for skin brightness (L* value) with a color difference meter (CR-300, Konica Minolta Inc.), and the difference between the L* value of the applied site of the comparative cosmetic 1 (control) and the L* value of the applied site of the skin-whitening cosmetic 1 or the comparative cosmetic 2 or 3 was calculated (ΔL* value=L* value of the applied site of the skin-whitening cosmetic 1 (or the comparative cosmetic 2 or 3)−L* value of the applied site of the comparative cosmetic 1). The greater the degree of pigmentation is, the lower the L* value is. Accordingly, it is possible to determine that the larger the ΔL* value is, the more improved the pigmentation has been. The calculated ΔL* value of 0.4 or more was determined to be A, and less than 0.4 to be B. The results are shown in Table 7.

TABLE 7

| | Formulation Concentration (% by mass) | L* value | ΔL* value | Determination |
|---|---|---|---|---|
| Skin-whitening cosmetic 1 | 1% | 63.92 | 0.40 | A |
| Comparative cosmetic 2 | 1% | 63.82 | 0.30 | B |
| Comparative cosmetic 3 | 2% | 63.85 | 0.33 | B |
| Comparative cosmetic 1 (Control) | — | 63.52 | — | — |

According to the results in Table 7, the skin-whitening cosmetic 1 of the present invention has a strong pigmentation inhibitory action, compared with the comparative cosmetic 2 and the comparative cosmetic 3, and this shows that the skin-whitening cosmetic 1 of the present invention exhibits an excellent skin-whitening effect (pigmentation improving effect). This is a skin-whitening effect by the melanogenesis inhibitor (D-pantothenyl alcohol) contained in the skin-whitening cosmetic 1 of the present invention. It can also be appreciated that since the melanogenesis inhibitor of the present invention also has a keratinocyte cell proliferation action in addition to the melanogenesis inhibitory action, it can achieve a higher skin-whitening effect compared with existing skin-whitening agents.

Reference Examples 1 to 64 (Skin-Whitening Cosmetics 5 to 68)

The skin-whitening cosmetic 5 formulated as shown in Table 8 below was prepared. In addition, the skin-whitening cosmetics 5 to 55 further containing in the formulation (A) the plant extracts shown in Table 1 at a concentration of 1.0% by mass relative to the total amount of the cosmetic were prepared. In addition, the plant extracts were replaced with "4-n-butyl resorcinol", "ursolic acid phosphate ester", "2-hydroxy-2'-hydroxy-5,5'-dipropyl-1,1'-biphenyl", "disodium adenosine monophosphate", the aforementioned compounds 1, 2, 13, 30, 31, 33, 45, 47, or 49, to prepare the skin-whitening cosmetics 56 to 68. The concentrations of the "4-n-butyl resorcinol", "ursolic acid phosphate ester", compounds 1, 2, 13, 30, 31, 33, 45, 47, and 49 were 0.1% by mass relative to the total amount of the cosmetic, and the concentrations of the "2-hydroxy-2'-hydroxy-5,5'-dipropyl-1,1'-biphenyl", and "disodium adenosine monophosphate" were 1.0% by mass relative to the total amount of the cosmetic.

As a note, in the present experiment, 1-(triphenylmethyl)piperidine was synthesized by the method described in WO2010/074052 and was used for the compound 2, and 2-(triphenylmethyloxy)ethanol was synthesized by the method described in the same literature and was used for the compound 13. N-(pmethylbenzoyl)-L-serine was synthesized by the method described in WO2011/074643 and was used for the compound 30, and N-(p-methoxybenzoyl)-L-serine was synthesized by the method described in the same literature and was used for the compound 33. N-(toluyl)cysteic acid was synthesized by the method described in WO2010/058730 and was used for the compound 47, and N-(4-methoxybenzoyl)-L-cysteic acid was synthesized by the method described in the same literature and was used for the compound 49. The compounds 1, 31, and 45 are the same as in the aforementioned <Experiment 3>.

Any of the skin-whitening cosmetics 5 to 68 was obtained by the same preparation method as the cosmetic 1, in which the ingredients of (A) were combined and dissolved at room temperature, and the ingredients of (B) were dissolved at room temperature, added to the formulation (A), and solubilized.

TABLE 8

Skin-whitening Cosmetic 5

| | (lotion) | (parts by mass) |
|---|---|---|
| (A) | D-pantothenyl alcohol | 1.0 |
| | glycerin | 5.0 |
| | propylene glycol | 4.0 |
| | purified water | balance |
| (B) | POE(20) sorbitan monolaurate ester | 1.5 |
| | POE(20) lauryl ether | 0.5 |
| | ethanol | 10.0 |
| | perfume | 0.1 |
| | Total | 100.0 |

<Evaluation of Skin-Whitening Rate>

The aforementioned skin-whitening cosmetics 5 to 68 were evaluated for skin-whitening rate in accordance with the following procedure. The comparative cosmetic 4 was prepared in the same manner as the cosmetic 5 except that the D-pantothenyl alcohol formulated into the cosmetic 5 was replaced with water.

A total of eight 1.0 cm×1.0 cm sites were provided inside the right and left upper arms of a panelist who voluntarily participated. The provided sites were subjected to a minimal erythema dose (1MED) of ultraviolet irradiation once a day, three times for three consecutive days. The skin-whitening cosmetics 5 to 68 and the comparative cosmetic 4 were applied at 50 μL twice a day for 21 consecutive days after completion of the ultraviolet irradiation in Experiment Day 1 (after completion of the first irradiation). Twenty-four hours after completion of the second application of each day, each test site was measured for skin brightness (L* value) with a color difference meter (CR-300, Konica Minolta Inc.), and the difference between the L* value of the applied site of the comparative cosmetic 4 and the L* value of the applied site of the skin-whitening cosmetics 5 to 68 was calculated (ΔL* value=L* value of the applied site of the skin-whitening cosmetic 5 (or the skin-whitening cosmetics 6 to 68)–L* value of the applied site of the comparative cosmetic 4). The greater the degree of pigmentation is, the lower the L* value is. Accordingly, it is possible to determine that the larger the ΔL* value is, the more improved the pigmentation has been. The number of days taken for the calculated ΔL* value to become 0.4 and the ΔL* value measured/calculated 24 hours after completion of the application in Day 21 are shown in Tables 9 to 19.

Furthermore, the cosmetics 6' to 68' each were prepared in the same manner as the cosmetic 5 except that the D-pantothenyl alcohol formulated into the cosmetics 6 to 68 was replaced with water, in order to calculate the ΔL* value and the number of days taken for the ΔL* value to become 0.4 for the cosmetics 6 to 68 containing none of the skin-whitening ingredient D pantothenyl alcohol, i.e., containing only any of the aforementioned plant extract or an existing skin-whitening compound as a skin-whitening ingredient. Subsequently, in the same manner as in the aforementioned <Evaluation in Skin-Whitening Rate>, the comparative cosmetic 4 was used as a control, and the number of days taken for the ΔL* value to become 0.4 as well as the L* value and ΔL* value measured 24 hours after completion of the application in Day 21 was obtained. The ΔL* values measured/calculated 24 hours after completion of the application in Day 21 are shown as "ΔL* value for no D-pantothenyl alcohol" in Tables 9 to 19. The number of days taken for the ΔL* value to become 0.4 was more than 21 days in every case.

TABLE 9

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.41 | 21 | — |
| 6 | D-pantothenyl alcohol + plant extract 1 | 0.44 | 18 | 0.10 |
| 7 | D-pantothenyl alcohol + plant extract 2 | 0.43 | 19 | 0.08 |
| 8 | D-pantothenyl alcohol + plant extract 3 | 0.44 | 18 | 0.11 |
| 9 | D-pantothenyl alcohol + plant extract 4 | 0.44 | 19 | 0.12 |
| 10 | D-pantothenyl alcohol + plant extract 5 | 0.43 | 20 | 0.11 |
| 11 | D-pantothenyl alcohol + plant extract 6 | 0.42 | 20 | 0.08 |
| Comparative cosmetic 4 (Control) | — | — | — | — |

TABLE 10

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.40 | 21 | — |
| 12 | D-pantothenyl alcohol + plant extract 7 | 0.41 | 20 | 0.07 |
| 13 | D-pantothenyl alcohol + plant extract 8 | 0.41 | 20 | 0.07 |
| 14 | D-pantothenyl alcohol + plant extract 9 | 0.41 | 20 | 0.08 |
| 15 | D-pantothenyl alcohol + plant extract 10 | 0.41 | 20 | 0.09 |
| 16 | D-pantothenyl alcohol + plant extract 11 | 0.41 | 20 | 0.08 |
| 17 | D-pantothenyl alcohol + plant extract 12 | 0.41 | 20 | 0.10 |
| Comparative cosmetic 4 (Control) | — | — | — | — |

TABLE 11

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.40 | 21 | — |
| 18 | D-pantothenyl alcohol + plant extract 13 | 0.41 | 20 | 0.08 |
| 19 | D-pantothenyl alcohol + plant extract 14 | 0.41 | 20 | 0.08 |
| 20 | D-pantothenyl alcohol + plant extract 15 | 0.41 | 20 | 0.07 |
| 21 | D-pantothenyl alcohol + plant extract 16 | 0.41 | 20 | 0.08 |
| 22 | D-pantothenyl alcohol + plant extract 17 | 0.41 | 20 | 0.08 |
| 23 | D-pantothenyl alcohol + plant extract 18 | 0.41 | 20 | 0.07 |
| Comparative cosmetic 4 (Control) | — | — | — | — |

TABLE 12

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.41 | 21 | — |
| 24 | D-pantothenyl alcohol + plant extract 19 | 0.42 | 20 | 0.09 |
| 25 | D-pantothenyl alcohol + plant extract 20 | 0.42 | 20 | 0.07 |
| 26 | D-pantothenyl alcohol + plant extract 21 | 0.42 | 20 | 0.08 |
| 27 | D-pantothenyl alcohol + plant extract 22 | 0.42 | 20 | 0.08 |
| 28 | D-pantothenyl alcohol + plant extract 23 | 0.42 | 20 | 0.09 |
| 29 | D-pantothenyl alcohol + plant extract 24 | 0.42 | 20 | 0.07 |
| Comparative cosmetic 4 (Control) | — | — | — | — |

TABLE 13

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.40 | 21 | — |
| 30 | D-pantothenyl alcohol + plant extract 25 | 0.41 | 20 | 0.08 |
| 31 | D-pantothenyl alcohol + plant extract 26 | 0.41 | 20 | 0.09 |
| 32 | D-pantothenyl alcohol + plant extract 27 | 0.41 | 20 | 0.07 |
| 33 | D-pantothenyl alcohol + plant extract 28 | 0.41 | 20 | 0.08 |
| 34 | D-pantothenyl alcohol + plant extract 29 | 0.41 | 20 | 0.09 |
| 35 | D-pantothenyl alcohol + plant extract 30 | 0.41 | 20 | 0.07 |
| Comparative cosmetic 4 (Control) | — | — | — | — |

TABLE 14

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.40 | 21 | — |
| 36 | D-pantothenyl alcohol + plant extract 31 | 0.41 | 20 | 0.08 |
| 37 | D-pantothenyl alcohol + plant extract 32 | 0.41 | 20 | 0.10 |
| 38 | D-pantothenyl alcohol + plant extract 33 | 0.41 | 20 | 0.09 |
| 39 | D-pantothenyl alcohol + plant extract 34 | 0.41 | 20 | 0.08 |

TABLE 14-continued

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 40 | D-pantothenyl alcohol + plant extract 35 | 0.41 | 20 | 0.08 |
| 41 | D-pantothenyl alcohol + plant extract 36 | 0.40 | 21 | 0.10 |
| Comparative cosmetic 4 (Control) | — | — | — | — |

TABLE 15

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.40 | 21 | — |
| 42 | D-pantothenyl alcohol + plant extract 37 | 0.40 | 21 | 0.09 |
| 43 | D-pantothenyl alcohol + plant extract 38 | 0.40 | 21 | 0.07 |
| 44 | D-pantothenyl alcohol + plant extract 39 | 0.40 | 21 | 0.08 |
| 45 | D-pantothenyl alcohol + plant extract 40 | 0.40 | 21 | 0.09 |
| 46 | D-pantothenyl alcohol + plant extract 41 | 0.40 | 21 | 0.08 |
| 47 | D-pantothenyl alcohol + plant extract 42 | 0.40 | 21 | 0.08 |
| Comparative cosmetic 4 (Control) | — | — | — | — |

TABLE 16

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.40 | 21 | — |
| 48 | D-pantothenyl alcohol + plant extract 43 | 0.40 | 21 | 0.10 |
| 49 | D-pantothenyl alcohol + plant extract 44 | 0.40 | 21 | 0.08 |
| 50 | D-pantothenyl alcohol + plant extract 45 | 0.40 | 21 | 0.05 |
| 51 | D-pantothenyl alcohol + plant extract 46 | 0.40 | 21 | 0.10 |
| 52 | D-pantothenyl alcohol + plant extract 47 | 0.40 | 21 | 0.10 |
| 53 | D-pantothenyl alcohol + plant extract 48 | 0.40 | 21 | 0.06 |
| Comparative cosmetic 4 (Control) | — | — | — | — |

TABLE 17

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.40 | 21 | — |
| 54 | D-pantothenyl alcohol + plant extract 49 | 0.40 | 21 | 0.05 |
| 55 | D-pantothenyl alcohol + plant extract 50 | 0.40 | 21 | 0.10 |
| 56 | D-pantothenyl alcohol + 4-n-butyl resorcinol | 0.43 | 18 | 0.35 |
| 57 | D-pantothenyl alcohol + ursolic acid phosphate ester | 0.43 | 19 | 0.20 |
| 58 | D-pantothenyl alcohol + 2-hydroxy-2'-hydroxy-5,5'-dipropyl-1,1'-biphenyl | 0.38 | 21 | 0.29 |
| 59 | D-pantothenyl alcohol + disodium adenosine monophosphate | 0.38 | 21 | 0.33 |
| Comparative cosmetic 4 (Control) | — | — | — | — |

TABLE 18

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.41 | 21 | — |
| 60 | D-pantothenyl alcohol + Compound 1 | 0.44 | 18 | 0.35 |
| 61 | D-pantothenyl alcohol + Compound 2 | 0.46 | 17 | 0.38 |
| 62 | D-pantothenyl alcohol + Compound 13 | 0.44 | 18 | 0.35 |
| 63 | D-pantothenyl alcohol + Compound 30 | 0.45 | 18 | 0.35 |
| 64 | D-pantothenyl alcohol + Compound 31 | 0.43 | 18 | 0.34 |
| 65 | D-pantothenyl alcohol + Compound 33 | 0.44 | 18 | 0.34 |

TABLE 18-continued

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| Comparative cosmetic 4 (Control) | — | — | — | — |

TABLE 19

| Skin-whitening Cosmetic | Skin-whitening Ingredient | ΔL* Value | No. of Days Taken for ΔL* Value = 0.4 | ΔL* Value for No D-pantothenyl Alcohol |
|---|---|---|---|---|
| 5 | D-pantothenyl alcohol | 0.40 | 21 | — |
| 66 | D-pantothenyl alcohol + Compound 45 | 0.43 | 18 | 0.34 |
| 67 | D-pantothenyl alcohol + Compound 47 | 0.46 | 17 | 0.38 |
| 68 | D-pantothenyl alcohol + Compound 49 | 0.44 | 18 | 0.34 |
| Comparative cosmetic 4 (Control) | — | — | — | — |

From the results in Tables 9 to 19, it can be appreciated that a skin-whitening effect is obtained more quickly by applying to the skin a combination of D-pantothenyl alcohol and a specific plant extract or a specific existing skin-whitening compound. This is considered to be because D-pantothenyl alcohol has a skin-whitening action based on the two action mechanisms of inhibiting melanogenesis and promoting melanin discharge as well.

What is claimed is:

1. A skin-whitening cosmetic comprising D-pantothenyl alcohol and one or more selected from the following skin-whitening agents (A) to (D), wherein the combination of D-pantothenyl alcohol and the skin-whitening agent selected from (A) to (D) provides synergistic skin-whitening effects:

(A) a 4-butyl resorcinol;

(B) one or more selected from the following compounds 1, 2, 13, 30, 31, 33, 45, 47 and 49:

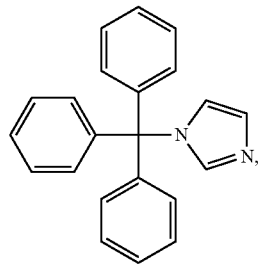
(Compound 1)

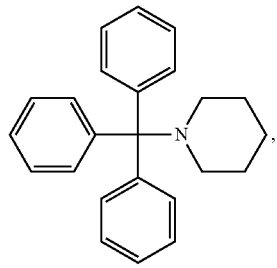
(Compound 2)

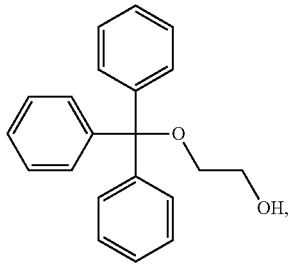
(Compound 13)

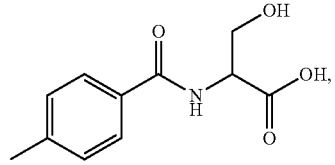
(Compound 30)

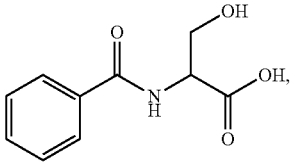
(Compound 31)

(Compound 33)

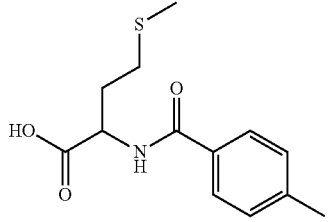
(Compound 45)

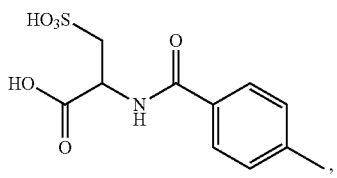
(Compound 47)

-continued

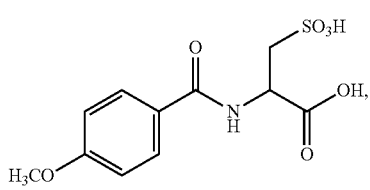
(Compound 49)

(C) an ursolic acid phosphate ester; and
(D) a salt of the (A), (B) or (C).

2. A skin-whitening method, comprising the steps of whitening skin by contacting D-pantothenyl alcohol with the skin; and whitening the skin by contacting one or more selected from the group consisting of the following skin-whitening agents (A) to (D) with the skin, wherein the combination of D-pantothenyl alcohol and the skin-whitening agent selected from (A) to (D) provides synergistic skin-whitening effects:

(A) a 4-butyl resorcinol;
(B) one or more selected from the following compounds 1, 2, 13, 30, 31, 33, 45, 47 and 49:

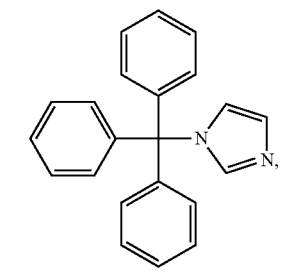
(Compound 1)

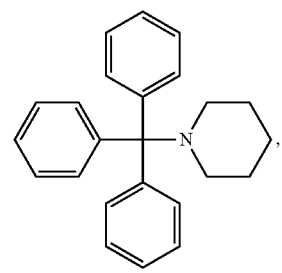
(Compound 2)

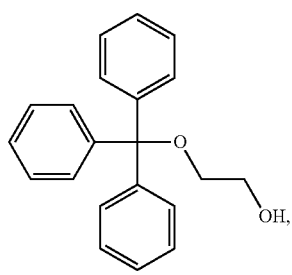
(Compound 13)

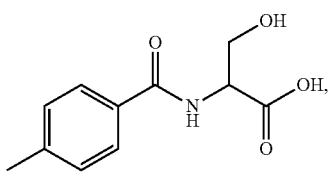
(Compound 30)

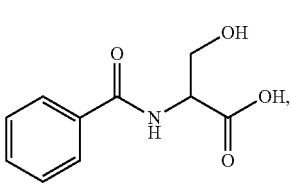
(Compound 31)

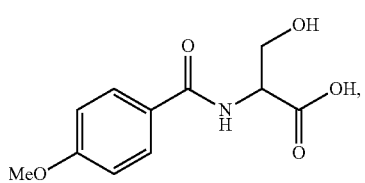
(Compound 33)

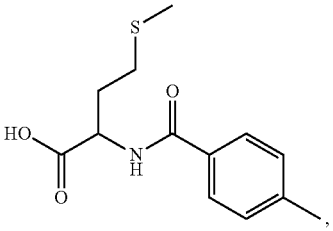
(Compound 45)

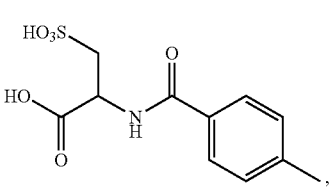
(Compound 47)

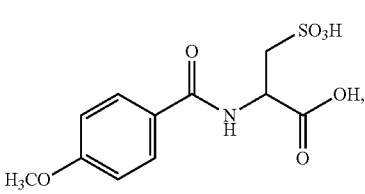
(Compound 49)

(C) an ursolic acid phosphate ester; and
(D) a salt of (A), (B) or (C).

3. The skin-whitening cosmetic according to claim 1, wherein the content of skin whitening agent selected from (A) to (D) in the skin-whitening cosmetic is 0.1 to 3% by mass.

4. The skin-whitening cosmetic according to claim 1, wherein the skin whitening agent (B) is one or more selected from the following compounds 1, 31, and 45:

5. The skin-whitening cosmetic method according to claim 2, wherein the skin whitening agent (B) is one or more selected from the following compounds 1, 31, and 45:
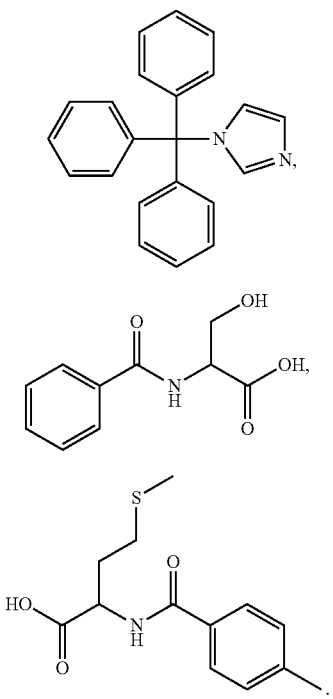
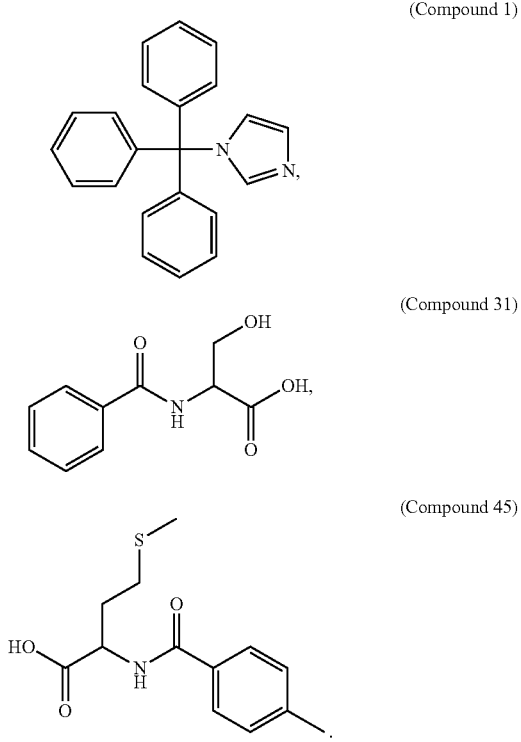
* * * * *

UNITED STATES PATENT AND TRADEMARK OFFICE
CERTIFICATE OF CORRECTION

PATENT NO. : 10,568,822 B2
APPLICATION NO. : 15/129391
DATED : February 25, 2020
INVENTOR(S) : Chihiro Kondo It is certified that error appears in the above-identified patent and that said Letters Patent is hereby corrected as shown below:

In the Specification

Column 4, Line 24, delete "esclentus" and insert -- esculentus --.

Column 4, Line 28, delete "aurantifolia" and insert -- aurantiifolia --.

Column 4, Line 29, delete "dulsis" and insert -- dulcis --.

Column 4, Line 36, delete "scariola" and insert -- serriola --.

Column 17, Table 1, Line 66, delete "esclentus" and insert -- esculentus --.

Column 18, Table 1, Line 8, delete "exract" and insert -- extract --.

Column 18, Table 10, Line 10, delete "aurantifolia" and insert -- aurantiifolia --.

Column 18, Table 10, Line 8, delete "dulsis" and insert -- dulcis --.

Column 18, Table 10, Line 24, delete "scariola" and insert -- serriola --.

Column 21, Line 31, delete "dulsis" and insert -- dulcis --.

Column 21, Line 54, delete "milefolium" and insert -- millefolium --.

Column 22, Line 19, delete "scariola" and insert -- serriola --.

Column 23, Line 24, delete "(POE-sorbit" and insert -- POE-sorbitan --.

Signed and Sealed this
Tenth Day of November, 2020

Andrei Iancu
*Director of the United States Patent and Trademark Office*

Column 23, Line 33, delete "glucosides" and insert -- glucosides. --.

Column 27, Line 18, delete "(pmethylbenzoyl)" and insert -- (p-methylbenzoyl) --.